US009062014B2

(12) United States Patent
Bonham et al.

(10) Patent No.: US 9,062,014 B2
(45) Date of Patent: Jun. 23, 2015

(54) CRYSTALLINE FORMS OF (R)-5-[3-CHLORO-4-(2,3-DIHYDROXY-PROPOXY)-BENZ[Z]YLIDENE]-2-([Z]-PROPYLIMINO)-3-O-TOLYL-THIAZOLIDIN-4-ONE

(75) Inventors: Nicholas Bonham, Oxford (GB);
Stephan Buchmann, Allschwil (CH);
Alex Eberlin, Cambridge (GB);
Christoph Imboden, Hofstetten (CH);
Markus Von Raumer, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 930 days.

(21) Appl. No.: 13/125,102

(22) PCT Filed: Oct. 19, 2009

(86) PCT No.: PCT/IB2009/054592
§ 371 (c)(1),
(2), (4) Date: Apr. 20, 2011

(87) PCT Pub. No.: WO2010/046835
PCT Pub. Date: Apr. 29, 2010

(65) Prior Publication Data
US 2011/0196004 A1 Aug. 11, 2011

(30) Foreign Application Priority Data
Oct. 20, 2008 (GB) .................................. 0819182.7

(51) Int. Cl.
*A61K 31/426* (2006.01)
*C07D 277/54* (2006.01)

(52) U.S. Cl.
CPC ............ *C07D 277/54* (2013.01); *A61K 31/426* (2013.01)

(58) Field of Classification Search
CPC ........................... A61K 31/426; C07D 277/42
USPC ............................................ 514/369; 548/184
See application file for complete search history.

(56) References Cited

U.S. PATENT DOCUMENTS

| | | | |
|---|---|---|---|
| 7,435,828 B2 | 10/2008 | Binkert et al. | |
| 7,626,037 B2 | 12/2009 | Binkert et al. | |
| 7,875,726 B2 | 1/2011 | Binkert et al. | |
| 8,263,780 B2 | 9/2012 | Abele et al. | |
| 8,273,779 B2 | 9/2012 | Binkert et al. | |
| RE43,728 E | 10/2012 | Binkert et al. | |
| RE43,833 E | 11/2012 | Binkert et al. | |
| 8,524,752 B2 | 9/2013 | Binkert et al. | |
| 8,785,484 B2 | 7/2014 | Brossard et al. | |
| RE45,174 E | 9/2014 | Binkert et al. | |
| 8,912,340 B2 | 12/2014 | Abele et al. | |
| 2007/0082933 A1 | 4/2007 | Bolli et al. | |
| 2007/0134803 A1 * | 6/2007 | Blatter et al. | .................... 436/96 |
| 2009/0275625 A1 | 11/2009 | Binkert et al. | |
| 2010/0317867 A1 | 12/2010 | Abele et al. | |
| 2011/0021581 A1 | 1/2011 | Brossard et al. | |
| 2012/0302758 A1 | 11/2012 | Abele et al. | |
| 2014/0303217 A1 | 10/2014 | Brossard et al. | |
| 2014/0315964 A1 | 10/2014 | Brossard et al. | |
| 2014/0316140 A1 | 10/2014 | Brossard et al. | |

FOREIGN PATENT DOCUMENTS

| | | | |
|---|---|---|---|
| JP | 2007-511563 | 5/2007 | |
| WO | WO 2005/054215 | 6/2005 | |
| WO | WO 2005054215 A1 * | 6/2005 | ........... C07D 277/20 |
| WO | WO 2008/062376 | 5/2008 | |
| WO | WO 2009/115954 | 9/2009 | |

OTHER PUBLICATIONS

Background Information for the October ACPS Meeting, FDA, 2002.*
B. Rodriquez-Spong et al. Advanced Drug Delivery Reviews, 2004, 56, pp. 241-274.*
Hilfiker, R. Polymorphism in the Pharmaceutical Industry, Wiley, 2006, 213-216.*
PCT/IB2009/054592 (Written Opinion), Actelion Pharmaceuticals Ltd.
Pharm. Tech. Japan, Ch. 18, vol. 10, pp. 1629-1644, (2002) (see Engl. Translation of Relevant Parts).
Maruzen, "Yuki Kagobutsu Kessyo Sakusei Handobukku (Handbook of Organic Compound Crystal Production)", p. 57-84 (2008) See Engl. Translation of Relevant Parts).
Byrn, S. et al., Pharmaceutical Research, vol. 12, No. 7, pp. 945-954, (1995).
Grant, D.J.W. et al., "Polymorphism in Pharmaceutical Solids", (Chapter 1), pp. 1-10, (1999).
Guillory, J.K., "Polymorphism in Pharmaceutical Solids", (Chapter 5), pp. 183-226, (1999).
U.S. Appl. No. 13/951,954, filed Jul. 26, 2013, Christoph Binkert et al.
U.S. Appl. No. 14/028,712, filed Sep. 17, 2013, Christoph Binkert et al.
PCT/IB2009/054592(Written Opinion), Actelion Pharmaceuticals Ltd.
Caira, M.R., "Crystalline Polymorphism of Organic Compounds", Topics in Current Chemistry, vol. 198, pp. 163-208, (1998).
Remington, The Science and Practice of Pharmacy, 21st Edition (2005), Part 5, "Pharmaceutical Manufacturing" [published by Lippincott Williams & Wilkins].
Braga, D., et al., "Dealing with Crystal Forms (The Kingdom of Serendip?)", Chemistry, An Asian Journal, vol. 6, pp. 2214-2223 (2011).

* cited by examiner

*Primary Examiner* — Joseph Kosack
*Assistant Examiner* — Matthew Coughlin
(74) *Attorney, Agent, or Firm* — Hoxie & Associates LLC

(57) ABSTRACT

The invention relates to crystalline forms of (R)-5-[3-chloro-4-(2,3-dihydroxy-propoxy)-benz[Z]ylidene]-2-([Z]-propylimino)-3-o-tolyl-thiazolidin-4-one, processes for the preparation thereof, pharmaceutical compositions containing said crystalline forms, and their use as compounds improving vascular function and as immunomodulating agents, either alone or in combination with other active compounds or therapies.

20 Claims, 3 Drawing Sheets

CRYSTALLINE FORMS OF (R)-5-[3-CHLORO-4-(2,3-DIHYDROXY-PROPOXY)-BENZ[Z]YLIDENE]-2-([Z]-PROPYLIMINO)-3-O-TOLYL-THIAZOLIDIN-4-ONE

CROSS REFERENCE TO RELATED APPLICATIONS

This application is a United States Application under 35 U.S.C. 371 claiming benefit of PCT Application No. PCT/IB2009/054592, filed on Oct. 19, 2009, which claims the benefit of GB Application No. 0819182.7 filed on Oct. 20, 2008.

The invention relates to crystalline forms of (R)-5-[3-chloro-4-(2,3-dihydroxy-propoxy)-benz[Z]ylidene]-2-([Z]-propylimino)-3-o-tolyl-thiazolidin-4-one (hereinafter also referred to as "COMPOUND"), processes for the preparation thereof, pharmaceutical compositions containing said crystalline forms, and their use as compounds improving vascular function and as immunomodulating agents, either alone or in combination with other active compounds or therapies.

BACKGROUND OF THE INVENTION

The preparation of (R)-5-[3-chloro-4-(2,3-dihydroxy-propoxy)-benz[Z]ylidene]-2-([Z]-propylimino)-3-o-tolyl-thiazolidin-4-one and the medicinal use thereof is described in the published PCT application WO 2005/054215.

It has now been surprisingly found that crystalline forms of (R)-5-[3-chloro-4-(2,3-dihydroxy-propoxy)-benz[Z]ylidene]-2-([Z]-propylimino)-3-o-tolyl-thiazolidin-4-one may under certain conditions be found, said crystalline forms having advantageous properties, especially compared to the amorphous COMPOUND as disclosed in WO 2005/054215. Such advantages may include better flow properties, higher thermodynamic stability, less hygroscopicity, different solubility, higher purity, better reproducibility in manufacturing (for example better filtration parameters and better reproducibility of formation of the solid), defined morphology, and/or better long-term stability.

Figure 1:
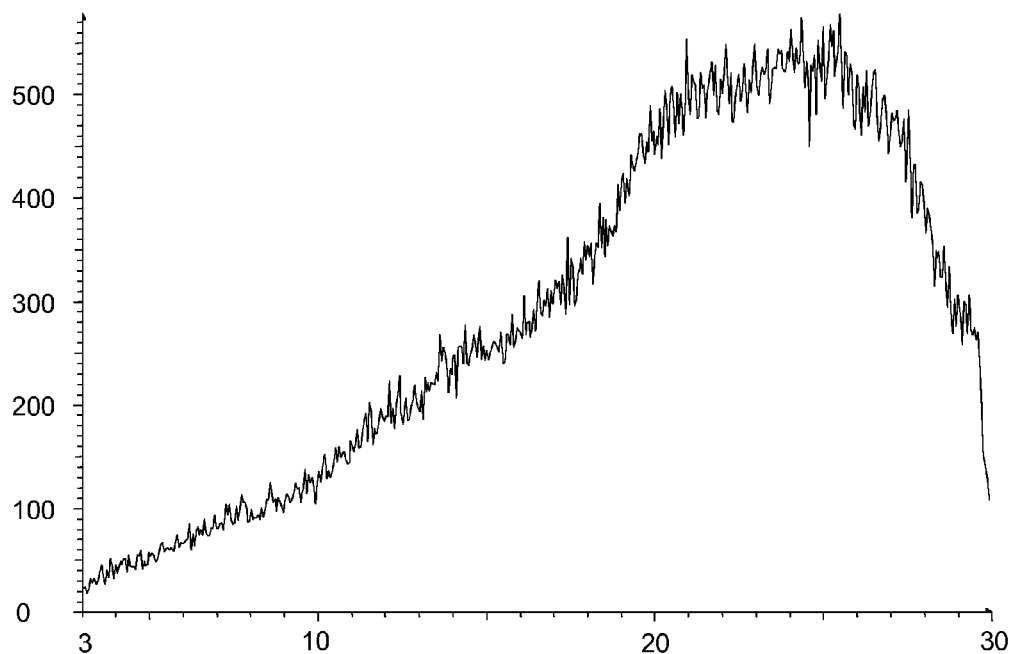
FIG. 1 shows the X-ray powder diffraction diagram of the COMPOUND in X-ray amorphous form.

In the X-ray diffraction diagrams of FIGS. 1, 2, 3, 4, and 5 the angle of refraction 2θ is plotted on the horizontal axis and the counts on the vertical axis.

Figure 2:
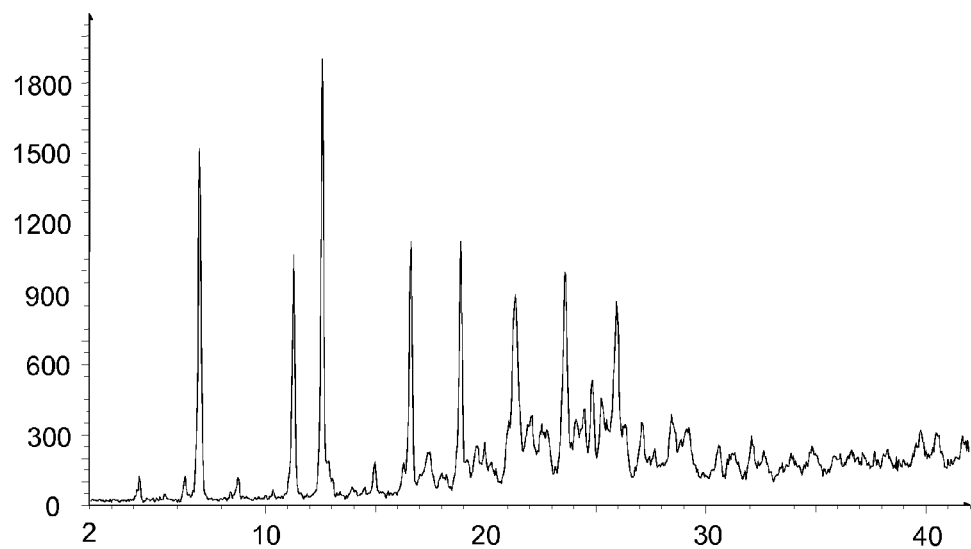
FIG. 2 shows the X-ray powder diffraction diagram of the COMPOUND in the crystalline form A as obtained from Example 1. The X-ray diffraction diagram shows peaks having a relative intensity, as compared to the most intense peak in the diagram, of the following percentages (relative peak intensitites given in parenthesis) at the indicated angles of refraction 2θ: 4.2° (6.2%), 6.3° (6.3%), 7.0° (79.8%), 8.7° (5.9%), 11.2° (56.0%), 12.6° (100.0%), 14.9° (9.5%), 16.6° (59.0%), 17.4° (11.7%), 18.8° (59.5%), 21.3° (47.0%), 23.6° (52.0%), 24.8° (28.3%), 26.0° (45.5%), 27.1° (19.0%), and 28.5° (21.0%).
Figure 3:
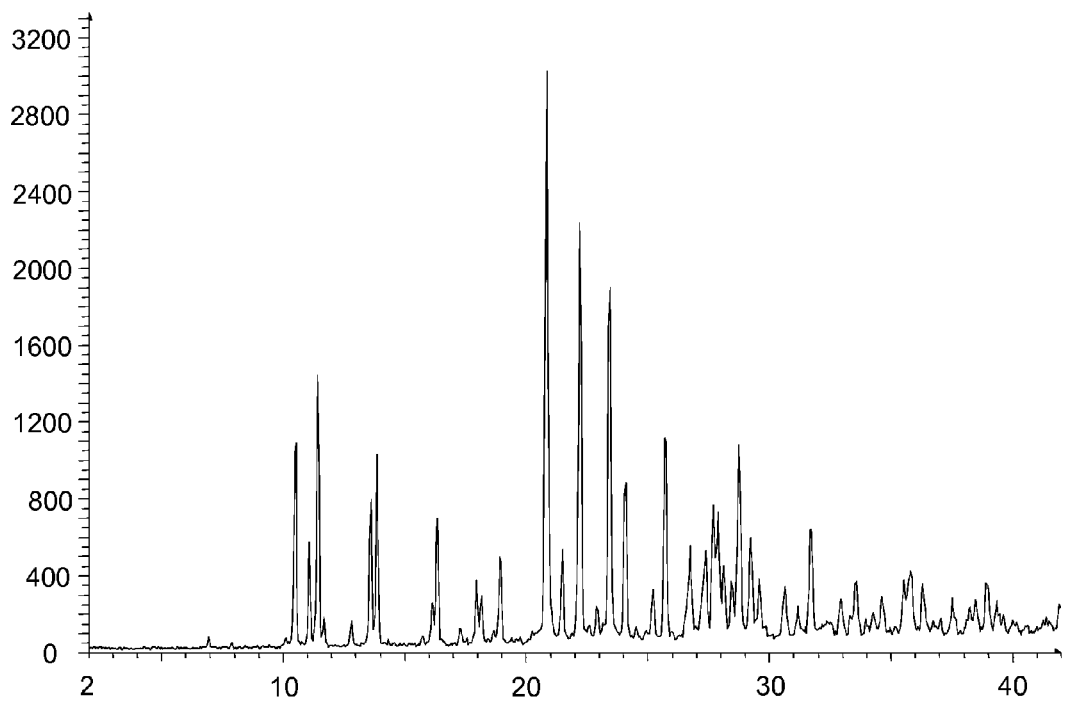
FIG. 3 shows the X-ray powder diffraction diagram of the COMPOUND in the crystalline form C as obtained from Example 2. The X-ray diffraction diagram shows peaks having a relative intensity, as compared to the most intense peak in the diagram, of the following percentages (relative peak intensitites given in parenthesis) at the indicated angles of refraction 2θ: 10.5° (36.3%), 11.1° (19.2%), 11.4° (47.9%), 13.6° (26.5%), 13.9° (34.2%), 16.3° (23.4%), 18.0° (12.3%), 18.2° (9.6%), 18.9° (16.7%), 20.8° (100.0%), 21.5° (18.5%), 22.2° (74.7%), 23.4° (63.2%), 24.1° (29.8%), 25.7° (37.3%), 26.8° (18.4%), 27.4° (17.4%), 27.7° (25.4%), 27.9° (24.1%), 28.7° (36.8%), 29.3° (19.6%), and 31.7° (21.8%).
Figure 4:
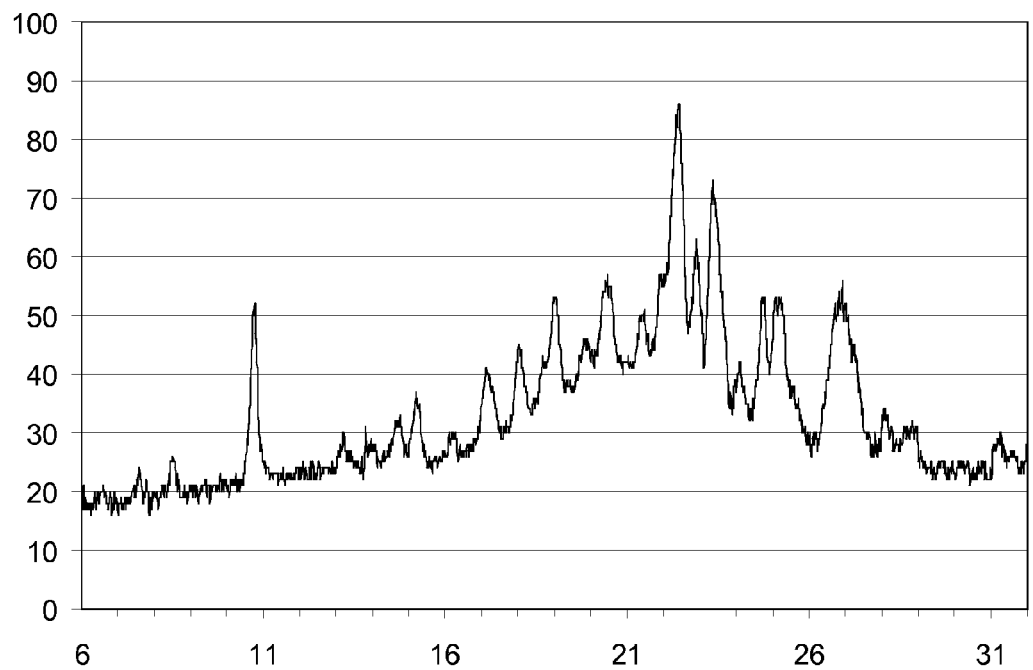
FIG. 4 shows the X-ray powder diffraction diagram measured with method 2 of the COMPOUND in the crystalline form III as obtained from Example 3. The X-ray diffraction diagram shows peaks having a relative intensity, as compared to the most intense peak in the diagram, of the following percentages (relative peak intensitites given in parenthesis) at the indicated angles of refraction 2θ (only selected peaks are stated): 8.5° (30%), 10.7° (59%), 14.7° (37%), 15.2° (42%), 18.0° (52%), 22.4° (100%), 23.4° (85%), and 26.9° (62%).
Figure 5:
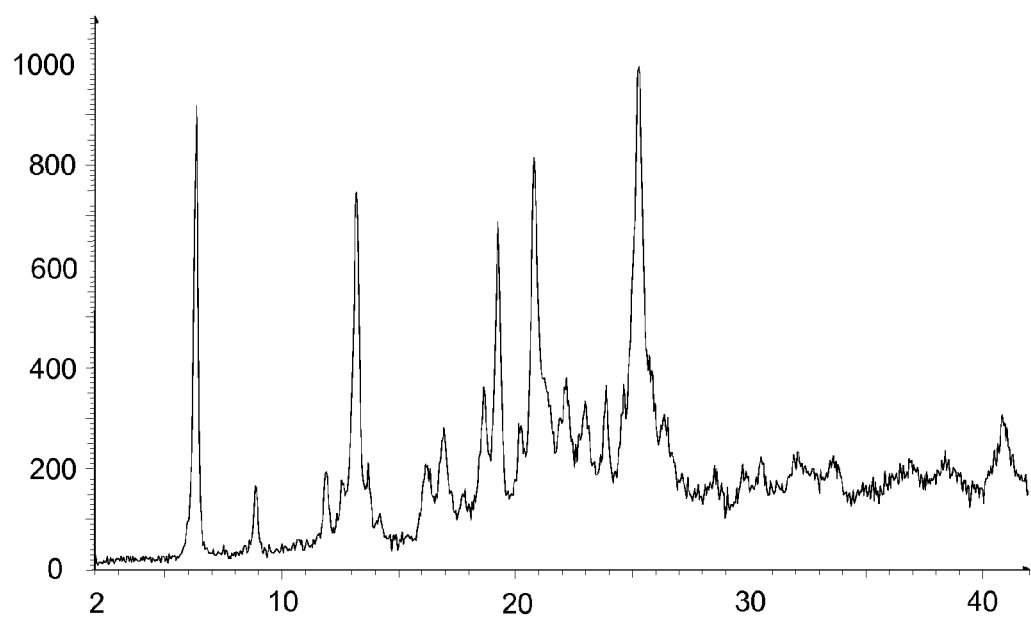
FIG. 5 shows the X-ray powder diffraction diagram of the COMPOUND in the crystalline form II as obtained from Example 4. The X-ray diffraction diagram shows peaks having a relative intensity, as compared to the most intense peak in the diagram, of the following percentages (relative peak intensitites given in parenthesis) at the indicated angles of refraction 2θ: 6.4° (92.3%), 8.9° (16.5%), 11.9° (19.3%), 13.2° (75.0%), 16.9° (28.0%), 18.6° (37.0%), 19.3° (70.1%), 20.8° (82.6%), and 25.3° (100.0%).

DETAILED DESCRIPTION OF THE INVENTION i) The present invention relates to a crystalline form, such as an essentially pure crystalline form, of the compound (R)-5-[3-chloro-4-(2,3-dihydroxy-propoxy)-benz[Z]ylidene]-2-([Z]-propylimino)-3-o-tolyl-thiazolidin-4-one containing from 0 to 2 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one.

ii) In another embodiment the present invention relates to a crystalline form according to embodiment i) containing from 0 to 1 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one.

iii) In another embodiment the present invention relates to a crystalline form according to embodiment i) containing from 0 to 0.5 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one.

iv) In another embodiment the present invention relates to a crystalline form according to embodiment i) containing 0.5 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one.

v) In another embodiment the present invention relates to a crystalline form according to embodiment i), wherein the compound (R)-5-[3-chloro-4-(2,3-dihydroxy-propoxy)-benz[Z]ylidene]-2-([Z]-propylimino)-3-o-tolyl-thiazolidin-4-one is in anhydrous form.

vi) In another embodiment the present invention relates to a crystalline form according to any one of embodiments i) to iii) containing from 0.1 to 2 equivalents of propionic acid per equivalent of (R)-5-[3-chloro-4-(2,3-dihydroxy-propoxy)-benz[Z]ylidene]-2-([Z]-propylimino)-3-o-tolyl-thiazolidin-4-one.

vii) In another embodiment the present invention relates to a crystalline form according to any one of embodiments i) to iv), characterised by the presence of peaks in the X-ray powder diffraction diagram at the following angles of refraction 2θ: 7.0°, 11.2°, and 12.6°.

viii) In another embodiment the present invention relates to a crystalline form according to any one of embodiments i) to iii), and v), characterised by the presence of peaks in the X-ray powder diffraction diagram at the following angles of refraction 2θ: 10.5°, 22.2°, and 23.4°.

ix) In another embodiment the present invention relates to a crystalline form according to any one of embodiments i) to iii) and vi), characterised by the presence of peaks in the X-ray powder diffraction diagram at the following angles of refraction 2θ: 10.7°, 15.2°, and 22.4°.

x) In another embodiment the present invention relates to a crystalline form according to any one of embodiments i) to iii), and v), characterised by the presence of peaks in the X-ray powder diffraction diagram at the following angles of refraction 2θ: 6.4°, 13.2°, and 25.3°.

xi) In another embodiment the present invention relates to a crystalline form according to any one of embodiments i) to iv), characterised by the presence of peaks in the X-ray powder diffraction diagram at the following angles of refraction 2θ: 7.0°, 11.2°, 12.6°, 16.6°, 18.8°, 21.3°, 23.6°, and 26.0°.

xii) In another embodiment the present invention relates to a crystalline form according to any one of embodiments i) to iii), and v), characterised by the presence of peaks in the X-ray powder diffraction diagram at the following angles of refraction 2θ: 10.5°, 11.1°, 11.4°, 13.6°, 13.9°, 16.3°, 20.8°, 22.2°, 23.4°, 24.1°, 25.7°, 27.7°, 27.9°, 28.7°, and 29.3°.

xiii) In another embodiment the present invention relates to a crystalline form according to any one of embodiments i) to iii) and vi), characterised by the presence of peaks in the X-ray powder diffraction diagram at the following angles of refraction 2θ: 8.5°, 10.7°, 14.7°, 15.2°, 18.0°, 22.4°, and 23.4°.

xiv) In another embodiment the present invention relates to a crystalline form according to any one of embodiments i) to iii), and v), characterised by the presence of peaks in the X-ray powder diffraction diagram at the following angles of refraction 2θ: 6.4°, 13.2°, 16.9°, 18.6°, 19.3°, 20.8°, and 25.3°.

xv) In another embodiment the present invention relates to a crystalline form according to any one of embodiments i) to iv), which essentially shows the X-ray powder diffraction pattern as depicted in FIG. 2.

xvi) In another embodiment the present invention relates to a crystalline form according to any one of embodiments i) to iii), and v), which essentially shows the X-ray powder diffraction pattern as depicted in FIG. 3.

xvii) In another embodiment the present invention relates to a crystalline form according to any one of embodiments i) to iii) and vi), which essentially shows the X-ray powder diffraction pattern as depicted in FIG. 4.

xviii) In another embodiment the present invention relates to a crystalline form according to any one of embodiments i) to iii), and v), which essentially shows the X-ray powder diffraction pattern as depicted in FIG. 5.

xix) In another embodiment the present invention relates to a crystalline form according to any one of embodiments i) to iv), vii), xi), and xv), which has a melting point of about 113° C. as determined by differential scanning calorimetry using the method as described herein.

xx) In another embodiment the present invention relates to a crystalline form according to any one of embodiments i) to iii), v), viii), xii), and xvi), which has a melting point of about 133° C. as determined by differential scanning calorimetry using the method as described herein.

xxi) In another embodiment the present invention relates to a crystalline form according to any one of embodiments i) to iii), v), x), xiv), and xviii), which has a melting point of about 101° C. as determined by differential scanning calorimetry using the method as described herein.

xxii) In another embodiment the present invention relates to the crystalline form A according to any one of embodiments i) to iv), vii), xi), xv), and xix) obtainable by:

i) dissolving amorphous (R)-5-[3-chloro-4-(2,3-dihydroxy-propoxy)-benz[Z]ylidene]-2-([Z]-propylimino)-3-o-tolyl-thiazolidin-4-one (251.1 g) in acetonitrile (1.25 L) by heating;
ii) equilibrating the internal temperature at 58° C. with paddle stirring at 350 rpm;
iii) adding deionised water (1.0 L) in 250 mL aliquots (minimum internal temperature=45° C.) yielding a clear solution on mixing;
iv) allowing the internal temperature to reach 55° C. and adding one additional aliquot of water (250 mL) yielding a clear solution on mixing;
v) allowing the solution temperature to equilibrate at 59.5-60° C.;
vi) cooling the solution to 12° C. over about 2 hours (cooling rate=0.4° C./min); and
vii) stirring the suspension at 12° C. for 18 hours.

xxiii) In another embodiment the present invention relates to the crystalline form C according to any one of embodiments i) to iii), v), viii), xii), xvi), and xx) obtainable by:

i) suspending the crystalline form A of (R)-5-[3-chloro-4-(2,3-dihydroxy-propoxy)-benz[Z]ylidene]-2-([Z]-propylimino)-3-o-tolyl-thiazolidin-4-one (20.0 g) in tert-butyl methyl ether (100 mL);
ii) stirring with a mechanical stirrer at room temperature yielding a highly viscous paste that transforms to a thin fluid suspension of distinct yellow colour after stirring for 40 hours; and
iii) filtering off the solid and drying the same for 4 hours under vaccum at room temperature.

xxiv) In another embodiment the present invention relates to the crystalline form III according to any one of embodiments i) to iii), vi), ix), xiii), and xvii) obtainable by:

i) adding 1 mL propionic acid to crystalline form A of (R)-5-[3-chloro-4-(2,3-dihydroxy-propoxy)-benz[Z]ylidene]-2-([Z]-propylimino)-3-o-tolyl-thiazolidin-4-one (0.5 g);
ii) shaking the sample to completely dissolve all solid;
iii) keeping the sample overnight at room temperature; and
iv) filtering off the resulting solid.

xxv) In another embodiment the present invention relates to the crystalline form II according to any one of embodiments i) to iii), v), x), xiv), xviii), and xxi) obtainable by:

i) storing crystalline form III of (R)-5-[3-chloro-4-(2,3-dihydroxy-propoxy)-benz[Z]ylidene]-2-([Z]-propylimino)-3-o-tolyl-thiazolidin-4-one under high vaccum (<0.1 mbar) for one week; and
ii) storing the product open at room temperature and about 40% relative humidity overnight.

The term "essentially pure" is understood in the context of the present invention to mean especially that at least 90, preferably at least 95, and most preferably at least 99 percent by weight of the crystals of a COMPOUND are present in a crystalline form according to the present invention, especially in a single crystalline form of the present invention.

When defining the presence of peak in e.g. an X-ray powder diffraction diagram, a common approach is to do this in terms of the S/N ratio (S=signal, N=noise).

According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 2, FIG. 3, FIG. 4, and FIG. 5, respectively, the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

The crystalline forms of the present invention can be used as medicaments, e.g. in the form of pharmaceutical compositions for enteral or parenteral administration, such as especially oral administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the crystalline forms of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

The crystalline forms of COMPOUND may be used as single component or as mixtures with other crystalline forms or the amorphous form of COMPOUND.

Diseases or disorders associated with an activated immune system which can be treated and/or prevented with the crystalline forms of the present invention are described for example in WO 2005/054215.

Preferred diseases or disorders to be treated and/or prevented with the crystalline forms of the present invention are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

Particularly preferred diseases or disorders to be treated and/or prevented with the crystalline forms of the present invention are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the crystalline forms of the present invention are selected from multiple sclerosis and psoriasis.

The present invention also relates to a method for the prevention or treatment of a disease or disorder mentioned herein or mentioned in WO 2005/054215 comprising administering to a subject a pharmaceutically active amount of a crystalline form of the present invention.

Furthermore, the crystalline forms of the present invention are also useful in combination with one or several immunomodulating agents, for the prevention and/or treatment of the diseases and disorders mentioned herein. According to a preferred embodiment of the invention, said agents are selected from the group consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors.

The present invention also relates to the use of the crystalline forms of the present invention for the preparation of a pharmaceutical composition, optionally for use in combination with one or several immunomodulating agents, for the prevention or treatment of the diseases and disorders mentioned herein or mentioned in WO 2005/054215.

(R)-5-[3-Chloro-4-(2,3-dihydroxy-propoxy)-benz[Z]ylidene]-2-([Z]-propylimino)-3-o-tolyl-thiazolidin-4-one can be prepared for example as described in the published PCT application WO 2005/054215 (see in particular Example 85) or by using the preparation process as disclosed in the published PCT application WO 2008/062376.

EXPERIMENTAL PART

The following Examples illustrate the invention in more detail. Temperatures are given in degrees Celsius. If not stated otherwise, room temperature is in the range of 18-25° C., and percentages are given by weight.

Abbreviations As Used Herein:
ca. about
DSC differential scanning calorimetry
Fig. figure
$^1$H-NMR hydrogen-1 nuclear magnetic resonance
HPLC high performance liquid chromatography
PTFE polytetrafluoroethylene
q.s. quantity sufficient
RH relative humidity
rt room temperature
rpm rotations per minute
RRT relative retention times indicating the ratio of the retention times of impurities to the retention time of the active ingredient
TBME tert-butyl methyl ether
TFA trifluoroacetic acid
TGA thermogravimetric analysis
XRPD X-ray powder diffraction
X-ray Powder Diffraction Analysis X-ray powder diffraction patterns for Amorphous COMPOUND and COMPOUND in crystalline forms A, C, and II (FIGS. 1-3 and 5) were collected on a Bruker AXS/Siemens D5000 diffractometer using Cu Kα radiation (40 kV, 40 mA), θ-θ goniometer, automatic divergence and receiving slits, a graphite secondary monochromator and a scintillation counter. The instrument is performance checked using a certified Corundum standard (NIST 1976). Samples run under ambient conditions were prepared as flat plate specimens using powder as received. Approximately 35 mg of the sample was gently packed into a cavity cut into polished, zero-background (510) silicon wafer. The sample was rotated in its own plane during analysis. The data were collected over an angular range of 2° to 42° 2θ in continuous scan mode using a step size of 0.02° 2θ and a step time of 1 second. Diffraction data are reported using Cu Kα1 (λ=1.5406 Å), after the Kα2 component has been stripped using the instrument evaluation software (EVA). The accuracy of the 2θ values as provided herein is in the range of +/−0.1-0.2° as it is generally the case for conventionally recorded X-ray powder diffraction patterns.

X-ray powder diffraction analysis method 2 used to produce the X-ray powder diffraction pattern for COMPOUND in crystalline form III (FIG. 4): X-ray powder diffraction patterns were collected on a Bruker D8 HTS X-ray diffractometer equipped with a GADDS HiStar detector operated with Cu Kα-radiation in reflection geometry. Typically, the X-ray tube was run at 40 kV/40 mA. The instrument is performance checked using a certified Corundum standard (NIST 1976). Samples run under ambient conditions were prepared as flat plate specimens using powder as received. Approximately 3 mg of the sample was gently pressed on a microscope slide. The data were collected over an angular range of 6° to 32° 2θ in 2 automatically merged and integrated frames using Bruker PILOT software with an acquisition time of 180 second per frame. Diffraction data are reported without Kα2 component stripping and the background signal has not been removed. The accuracy of the 2θ values as provided herein is in the range of +/−0.1-0.2°.

Differential Scanning Calorimetry

DSC data were collected on a TA Instruments Q1000 equipped with a 50 position auto-sampler. The instrument was calibrated for energy and temperature using certified indium. Typically 0.5-3 mg of each sample, in a pin-holed aluminium pan, was heated at 10° C. min$^{-1}$, unless stated otherwise, from 25° C. to 250° C. A nitrogen purge at 30 ml min$^{-1}$ was maintained over the sample. Onset temperatures are given as peak tangential onset temperatures whereas melting points are reported as peak temperatures.

Thermogravimetric Analysis

TGA data were collected on a TA Instruments Q500 TGA, equipped with a 16 position auto-sampler. The instrument was temperature calibrated using certified Alumel. Typically 3-10 mg of each sample was loaded onto a pre-tared platinum crucible and aluminium DSC pan, and was heated at 10° C. min$^{-1}$ from room temperature to 350° C. A nitrogen purge at 60 ml min$^{-1}$ was maintained over the sample.

HPLC, Purity Analysis

Purity analysis was performed on an Agilent HP1100 series system equipped with a diode array detector and using ChemStation software v9. Samples were protected from light with foil. The autosampler tray was kept at 4° C.

| Type of method | Reverse Phase; Gradient |
| --- | --- |
| Column: | Phenomenex Luna C18 (2) 5 μm 150 × 4.6 mm |
| Column Temperature (° C.): | 35 |
| Injection (μl): | 10 |
| Detection Wavelength (nm) | 250 |
| Flow Rate (mL/min): | 1.0 |
| Phase A: | Water:acetonitrile:TFA, 950:50:1 v/v/v |
| Phase B: | Water:acetonitrile:TFA, 50:950:1 v/v/v |
| Timetable: | Time (min) % Phase A % Phase B |

| Time (min) | % Phase A | % Phase B |
| --- | --- | --- |
| 0 | 80 | 20 |
| 25 | 50 | 50 |
| 40 | 25 | 75 |
| 45 | 10 | 10 |
| 45.2 | 80 | 20 |
| 50 | 80 | 20 |

Example 1

Preparation of Form A

Amorphous COMPOUND (251.1 g) is dissolved in acetonitrile (1.25 L) by heating, and the internal temperature is equilibrated at ca. 58° C. with paddle stirring at 350 rpm. Deionised water (1.0 L) is added in 250 mL aliquots (minimum internal temperature=45° C.) yielding a clear solution on mixing. The internal temperature is allowed to reach 55° C. and one additional aliquot of water (250 mL) is added: the solution gets clear on mixing. The solution temperature is allowed to equilibrate at 59.5-60° C. and the solution is cooled to 12° C. over ca. 2 hours (cooling rate=0.4° C./min). The suspension is stirred at 12° C. for 18 hours and a sample of the solid product is analysed by XRPD. The product is form A.

TABLE 1

Characterisation data for form A

| Technique | Data Summary | Remarks |
| --- | --- | --- |
| XRPD | Crystalline: exhibits preferred orientation due to the presence of large crystals | see FIG. 2 |
| $^1$H-NMR | Consistent with structure. No significant amount of residual solvent detected | |
| DSC | broad endotherm with an onset at about 33.6° C. (about 51 J/g), sharper endotherm with an onset at about 108° C. (about 65 J/g) which corresponds to a melt. Melting point of about 113° C. | see Table legend under 1) |
| TGA | 1.9% weight loss between ambient and about 60° C. (equivalent to 0.5 moles of water per mole of COMPOUND) and a 19.6% weight loss between 225 and 340° C. due to decomposition. | see Table legend under 1) |
| Microscopy | Birefringent rod-like crystals up to ca. 70 μm in length and irregular birefringent particles. Some agglomerates and/or fused particles are also observed | |
| Hot-Stage Microscopy | Melt observed between 104-119° C. | |
| HPLC Purity | 98.7% pure by area with impurities at RRT of 0.73 (0.17%), 0.96 (0.36%), 1.02 (0.35%) and 1.19 (0.22%). | |

Legend for Table 1:
1): The TGA thermogram of form A shows a 1.9% weight loss between ambient and about 60° C. (equivalent to 0.5 moles of water per mole of COMPOUND) and a 19.6% weight loss between 225 and 340° C. due to decomposition. The first weight loss corresponds to a broad endotherm in the DSC with an onset of about 33.6° C. A second, sharper endotherm is observed with an onset of about 108° C. which corresponds to a melt.

Amorphous Compound

Amorphous COMPOUND is obtainable by the process described for Example 85 of the published PCT application WO 2005/054215. Alternatively, COMPOUND in crystalline form A (501 mg) is dissolved in dichloromethane (5 mL). The solution is filtered through a 0.45 μm PTFE filter and the solvent is removed by rotary evaporation to yield a pale yellow foam. The solid is dried at 40° C. under high vacuum for one day to yield the product: NB-174-6-1 (herein also referred to as "Amorphous COMPOUND").

TABLE 2

Characterisation data for NB-174-6-1

| Technique | Data Summary | Remarks |
|---|---|---|
| XRPD | X-ray amorphous | see FIG. 1 |
| $^1$H-NMR | Consistent with structure. Contains about 0.5% w/w dichloromethane | — |

Example 2

Preparation of Form C

COMPOUND in crystalline form A (20.0 g) is suspended in TBME (100 mL) and stirred with a mechanical stirrer at rt. A highly viscous paste is obtained that transforms to a thin fluid suspension of distinct yellow color after stirring for 40 hours. The solid is filtered off and dried for 4 hours under vacuum at rt. The product is identified as Form C by XRPD.

TABLE 3

Characterisation data for form C

| Technique | Data Summary | Remarks |
|---|---|---|
| XRPD | Crystalline: exhibits preferred orientation due to the presence of large crystals | see FIG. 3 |
| $^1$H-NMR | Consistent with structure. Contains a trace of TBME | |
| DSC | Endotherm (melt): onset at about 128° C. (about 92 J/g). Melting point of about 133° C. | |
| TGA | Weight losses: ambient-250° C. (0.4%), 250-340° C. (15.0% - decomposition) | |
| Microscopy | Birefringent columnar/prism-like crystals up to ca. 200 µm in length and smaller, irregular birefringent particles. | |
| Hot-Stage Microscopy | Melt observed between 127-138° C. | |
| HPLC Purity | 98.3% pure by area with impurities at RRT of 0.73 (0.21%), 0.96 (0.39%), 1.02 (0.37%) and 1.19 (0.52%) | |

Example 3

Preparation of Form III

COMPOUND in crystalline form A (0.5 g) is dissolved in propionic acid (1 mL). A solid product forms within several hours at room temperature. Said solid is isolated by filtration and is COMPOUND in crystalline form III.

TABLE 4

Characterisation data for form III

| Technique | Data Summary | Remarks |
|---|---|---|
| XRPD | Crystalline | see FIG. 4 |

Example 4

Preparation of Form II

COMPOUND in crystalline form III is stored under high vacuum (<0.1 mbar) for 1 week and then stored open at about 40% relative humidity and room temperature overnight, yielding the COMPOUND in crystalline form II.

TABLE 5

Characterisation data for form II

| Technique | Data Summary | Remarks |
|---|---|---|
| XRPD | Crystalline | see FIG. 5 |
| $^1$H-NMR | Consistent with structure. Contains 0.04 moles of propionic acid per mole of COMPOUND | |
| DSC | Endotherms: onsets at about 82° C. (about 4.5 J/g) and about 96° C. (about 58 J/g). Melting point of about 101° C. | |
| TGA | Weight losses: ambient-75° C. (0.3%), 75-90° C. (0.3%), 90-250° C. (0.6%) and 250-340° C. (27.2% - decomposition) | |
| Microscopy | Birefringent rod/needle-like crystals up to ca. 40 µm in length and agglomerates, up to ca. 300 µm in length | |
| Hot-Stage Microscopy | Melt observed between 96-106° C. | |
| HPLC Purity | 98.4% pure by area with impurities at RRT of 0.73 (0.27%), 0.96 (0.30%), 1.02 (0.36%), 1.19 (0.17%) and 1.37 (0.16%) | |

Example 5

Hygroscopicity of COMPOUND in Crystalline Forms A, C, and II Compared to Amorphous COMPOUND Method:

Gravimetric Vapour Sorption (GVS)

Sorption isotherms are obtained using a Hiden IGASorp moisture sorption analyser, controlled by CFRSorp software. The sample temperature is maintained at 25° C. by a Huber re-circulating water bath. The humidity is controlled by mixing streams of dry and wet nitrogen, with a total flow rate of 250 ml·min$^{-1}$. The relative humidity is measured by a calibrated Vaisala RH probe (dynamic range of 0-95% RH), located near the sample. The weight change of the sample as a function of % RH is constantly monitored by the microbalance (accuracy±0.001 mg).

Typically 10-20 mg of sample is placed in a tared mesh stainless steel basket under ambient conditions. The sample is loaded and unloaded at 40% RH and 25° C. (typical room conditions).

A moisture sorption isotherm is performed as outlined below (2 scans giving 1 complete cycle). The standard isotherm is performed at 25° C. at 10% RH intervals over a 0-90% RH range.

| Parameters | Values |
|---|---|
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (ml · min$^{-1}$) | 250 |
| Temperature (° C.) | 25 |
| Stability (° C. · min$^{-1}$) | 0.05 |
| Minimum Sorption Time (hours) | 1 |
| Maximum Sorption Time (hours) | 6 |
| Mode | AF2 |
| Accuracy (%) | 98 |

The software uses a least squares minimisation procedure together with a model of the mass relaxation, to predict an asymptotic value. The measured mass relaxation value must be within 5% of that predicted by the software, before the next % RH value is selected. The minimum equilibration time is set to 1 hour and the maximum to 4 hours.

Hygroscopicity of Solid Forms:

Classification is done according to the European Pharmacopea Technical Guide (1999 edition) (e.g. slightly hygroscopic: increase in mass is less than 2% and equal to or greater than 0.2% mass/mass; hygroscopic: increase in mass is less than 15% and equal to or greater than 2% mass/mass). The mass change between 40% relative humidity and 80% relative humidity in the first adsorption scan is considered.

Amorphous: 2.1% mass gain: Hygroscopic
Form A: <0.2% mass gain: Non-hygroscopic
Form C: <0.2% mass gain: Non-hygroscopic
Form II: 0.2% mass gain: Slightly hygroscopic Example 6

Capsules Containing 10 mg, 20 mg, or 40 mg of COMPOUND in Crystalline Form A or C

| Ingredients | Amount per capsule [mg] | | |
|---|---|---|---|
| Intragranular | | | |
| COMPOUND in crystalline form A or C | 10.00 mg | 20.00 mg | 40 mg |
| Pregelatinised starch | 168.00 mg | 158.00 mg | 138.00 mg |
| Polyvinylpyrrolidone | | 6.25 mg (2.5% w/w) | |
| Microcrystalline cellulose | | 50.00 mg (20% w/w) | |
| Sodium starch glycollate | | 5.00 mg (2% w/w) | |
| Sodium lauryl sulfate | | 2.50 mg (1% w/w) | |
| Granulating Fluid | | | |
| Purified water | | q.s. | |
| Extra-granular | | | |
| Sodium starch glycollate | | 5.00 mg (2% w/w) | |
| Silica colloidal anhydrous | | 0.75 mg (0.3% w/w) | |
| Magnesium Stearate | | 2.50 mg (1% w/w) | |
| Total | | 250 mg | |

The intragranular materials are sieved in a high shear mixer e.g. a Diosna where they are mixed together during the dry blending step. Water is added to the dry blend of intra-granular materials whilst mixing until suitable granules of suitable size are formed during the wet granulation step. The granules are then dried in a fluid bed dryer and milled using a screen of suitable porosity. All the extra-granular materials except magnesium stearate are passed through a 1000 μm screen and mixed with the granules. The magnesium stearate is then sieved together with a given amount of the previous blend and added to the rest of the powder blend. The final mixture is further blended. The powder is then filled in size "0", white-opaque hard gelatine capsules.

Example 7

Tablets Containing COMPOUND in crystalline Form C

| Excipients | Formula (% w/w) |
|---|---|
| Intragranular | |
| COMPOUND in crystalline form C | 16.0 |
| Lactose | 35.0 |
| Microcrystalline cellulose | 17.5 |
| Polyvinyl pyrrolidone | 3.0 |
| Sodium lauryl sulphate | 1.0 |
| Croscarmellose sodium (Ac-di-sol) | 4.0 |
| Granulating Fluid | |
| Sodium lauryl sulphate | 1.0 |
| Purified water | q.s. |
| Extra-granular | |
| Microcrystalline cellulose | 17.5 |
| Croscarmellose sodium (Ac-di-sol) | 4.0 |
| Magnesium stearate | 0.5 |
| Colloidal silicon dioxide | 0.5 |
| Total | 100.0 |

The intragranular materials are sieved in a high shear mixer e.g. a Diosna where they are mixed together during the dry blending step. Water is added to the dry blend of intra-granular materials whilst mixing until suitable granules of suitable size are formed during the wet granulation step. The granules are then dried in a fluid bed dryer and milled using a screen of suitable porosity. All the extra-granular materials except magnesium stearate are passed through a 1000 μm screen and mixed with the granules. The magnesium stearate is then sieved together with a given amount of the previous blend and added to the rest of the powder blend. The final mixture is further blended. The powder is then transferred on suitable tabletting equipment for compression. The tablets are then coated with Opadry II brown at 4% w/w gain during coating.

The invention claimed is:

1. A crystalline form of the compound (R)-5-[3-chloro-4-(2,3-dihydroxy-propoxy)-benz[Z]ylidene]-2-([Z]-propylimino)-3-o-tolyl-thiazolidin-4-one containing from 0 to 0.5 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one, characterised by the presence of peaks in the X-ray powder diffraction diagram at the following angles of refraction 2θ: 7.0°, 11.2°, and 12.6°, wherein the X-ray powder diffraction diagram is obtained by using Cu Kα1 radiation (λ=1.5406 Å), and wherein the accuracy of the 2θ values is in the range of +/− 0.2°.

2. The crystalline form according to claim 1, characterized by the presence of peaks in the X-ray powder diffraction diagram at the following angles of refraction 2θ: 7.0°, 11.2°, 12.6°, 16.6°, 18.8°, 21.3°, 23.6°, and 26.0°, wherein the X-ray powder diffraction diagram is obtained by using Cu Kα1 radiation (λ=1.5406 Å).

3. The crystalline form according to claim 1, which has a melting point of about 113° C. as determined by differential scanning calorimetry.

4. The crystalline form according to claim 1 containing 0.5 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one.

5. The crystalline form according to claim 2 containing 0.5 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one.

6. The crystalline form according to claim 2, which has a melting point of about 113° C. as determined by differential scanning calorimetry.

7. The crystalline form according to claim 4, which has a melting point of about 113° C. as determined by differential scanning calorimetry.

8. The crystalline form according to claim 5, which has a melting point of about 113° C. as determined by differential scanning calorimetry.

9. A pharmaceutical composition comprising the crystalline form according to claim 1 and a pharmaceutically acceptable carrier.

10. A method of treatment or prophylaxis of rejection of transplanted organs selected from kidney, liver, heart and lung; or graft-versus-host diseases brought about by stem cell transplantation; or a method of treatment of any of the following disorders: autoimmune syndromes selected from rheumatoid arthritis, multiple sclerosis, psoriasis, psoriatic arthritis, Crohn's disease, and Hashimoto's thyroiditis; and atopic dermatitis, wherein said method comprises administering to a subject in need thereof an effective amount of the crystalline form according to claim 1.

11. A crystalline form of the compound (R)-5-[3-chloro-4-(2,3-dihydroxy-propoxy)-benz[Z]ylidene]-2-([Z]-propylimino)-3-o-tolyl-thiazolidin-4-one containing from 0 to 0.5 equivalents of $H_2O$ per equivalent of (R)-5-[3-chloro-4-(2,3-dihydroxy-propoxy)-benz[Z]ylidene]-2-([Z]-propylimino)-3-o-tolyl-thiazolidin-4-one, characterised by the presence of peaks in the X-ray powder diffraction diagram at the following angles of refraction 2θ: 10.5°, 22.2°, and 23.4°, wherein the X-ray powder diffraction diagram is obtained by using Cu Kα1 radiation (λ=1.5406 Å), and wherein the accuracy of the 2θ values is in the range of +/− 0.2°.

12. The crystalline form according to claim 11, characterised by the presence of peaks in the X-ray powder diffraction diagram at the following angles of refraction 2θ: 10.5°, 11.1°, 11.4°, 13.6°, 13.9°, 16.3°, 20.8°, 22.2°, 23.4°, 24.1°, 25.7°, 27.7°, 27.9°, 28.7°, and 29.3°, wherein the X-ray powder diffraction diagram is obtained by using Cu Kα1 radiation (λ=1.5406 Å).

13. The crystalline form according to claim 11, which has a melting point of about 133° C. as determined by differential scanning calorimetry.

14. The crystalline form according to claim 11, wherein the compound (R)-5-[3-chloro-4-(2,3-dihydroxy-propoxy)-benz[Z]ylidene]-2-([Z]-propylimino)-3-o-tolyl-thiazolidin-4-one is in anhydrous form.

15. The crystalline form according to claim 12, wherein the compound (R)-5-[3-chloro-4-(2,3-dihydroxy-propoxy)-benz[Z]ylidene]-2-([Z]-propylimino)-3-o-tolyl-thiazolidin-4-one is in anhydrous form.

16. The crystalline form according to claim 12, which has a melting point of about 133° C. as determined by differential scanning calorimetry.

17. The crystalline form according to claim 14, which has a melting point of about 133° C. as determined by differential scanning calorimetry.

18. The crystalline form according to claim 15, which has a melting point of about 133° C. as determined by differential scanning calorimetry.

19. A pharmaceutical composition comprising the crystalline form according to claim 11 and a pharmaceutically acceptable carrier.

20. A method of treatment or prophylaxis of rejection of transplanted organs selected from kidney, liver, heart and lung; or graft-versus-host diseases brought about by stem cell transplantation; or a method of treatment of any of the following disorders: autoimmune syndromes selected from rheumatoid arthritis, multiple sclerosis, psoriasis, psoriatic arthritis, Crohn's disease; and Hashimoto's thyroiditis; and atopic dermatitis, wherein said method comprises administering to a subject in need thereof an effective amount of the crystalline form according to claim 11.

* * * * *

UNITED STATES PATENT AND TRADEMARK OFFICE
CERTIFICATE OF CORRECTION

PATENT NO. : 9,062,014 B2
APPLICATION NO. : 13/125102
DATED : June 23, 2015
INVENTOR(S) : Nicholas Bonham et al.

Page 1 of 1

It is certified that error appears in the above-identified patent and that said Letters Patent is hereby corrected as shown below:

In the Claims

Claim 11, Column 13, Line 26, "1.5406 A" should be replaced with "1.5406 Å"

Claim 11, Column 13, Line 27, "2θ" should be replaced with "2θ"

Signed and Sealed this
Seventeenth Day of November, 2015

Michelle K. Lee
*Director of the United States Patent and Trademark Office*